United States Patent [19]

Laugharn et al.

[11] Patent Number: 4,946,603
[45] Date of Patent: Aug. 7, 1990

[54] ELECTRONEGATIVELY CHARGED BLOOD FILTER AND BLOOD CELL SEPARATION METHOD

[75] Inventors: James A. Laugharn, Cambridge; Denis Hammerton, Wayland; Timothy W. Towle, Burlington, all of Mass.

[73] Assignee: Crystal Diagnostics, Inc., Woburn, Mass.

[21] Appl. No.: 272,457

[22] Filed: Nov. 17, 1988

[51] Int. Cl.$^5$ .............................................. B01D 39/06
[52] U.S. Cl. .................................... 210/807; 210/496; 210/509; 422/101; 436/177
[58] Field of Search ............... 210/484, 496, 505, 506, 210/507, 508, 509, 767, 691, 807; 422/101; 436/177

[56] References Cited

U.S. PATENT DOCUMENTS

| | | | |
|---|---|---|---|
| 3,448,041 | 6/1969 | Swank | 210/927 |
| 3,552,925 | 1/1971 | Fetter | 422/56 |
| 3,552,928 | 1/1971 | Fetter | 422/56 |
| 4,189,382 | 2/1980 | Zine, Jr. | 210/789 |
| 4,246,107 | 1/1981 | Tanenaka et al. | 210/806 |
| 4,376,675 | 3/1983 | Perrotta | 210/509 |
| 4,477,575 | 10/1984 | Vogel et al. | 210/767 |
| 4,523,995 | 6/1985 | Pall et al. | 210/509 |
| 4,596,660 | 6/1986 | Hou | 210/505 |
| 4,701,267 | 10/1987 | Watanabe et al. | 210/505 |

OTHER PUBLICATIONS

Raistrick, J. H., *Filtration & Separation*, Mar./Apr., 1981, pp. 149–152.
Raistrick, J. H., *Filtration & Separation*, Nov./Dec., 1976, pp. 614–620.
Shackleton, R., *Filtration & Separation*, Nov./Dec., 1977, pp. 632–638.
Wnek, W., *Filtration & Separation*, May/Jun., 1974, pp. 237–242.
Yarar, B. and T. Ozgur, *Filtration & Separation*, Sep.-/Oct., 1976, pp. 443–446.
Fleming, A., *Filtration & Separation*, Sep./Oct., 1980, pp. 480–482.
*Electrical Phenomena at Interfaces*, 1984, pp. 199, 398–403, 412.

Primary Examiner—W. Gary Jones
Attorney, Agent, or Firm—David Prashker

[57] ABSTRACT

A unique blood filter matrix material is provided which is able to effectively separate whole blood into cellular and noncellular constituents, especially when the whole blood volume is 0.5 milliliters or less. The filter matrix presents an overall negative surface electrical charge to the whole blood and utilizes a mechanism of action to rapidly separate cells from plasma or serum.

20 Claims, 2 Drawing Sheets

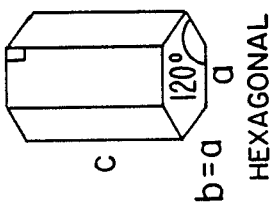
FIG.1d HEXAGONAL
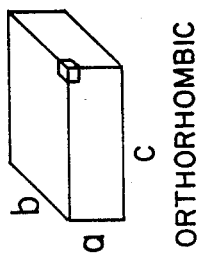
FIG.1c ORTHORHOMBIC
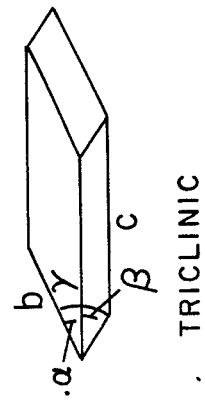
FIG.1g TRICLINIC
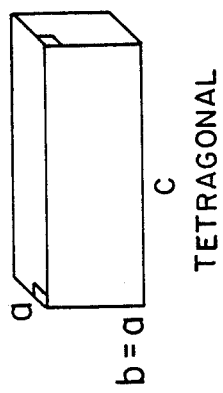
FIG.1b TETRAGONAL
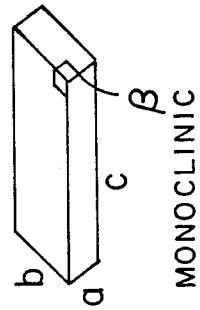
FIG.1f MONOCLINIC
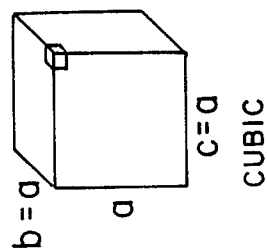
FIG.1a CUBIC
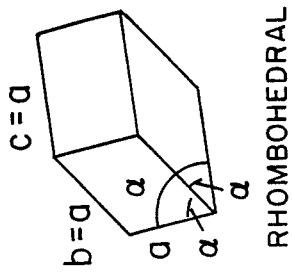
FIG.1e RHOMBOHEDRAL

ELECTRONEGATIVELY CHARGED BLOOD FILTER AND BLOOD CELL SEPARATION METHOD

FIELD OF THE INVENTION

The present invention is concerned with the effective separation of cellular and non-cellular constituents of blood into individual fractions; and is directly concerned with the rapid separation and recovery of plasma or serum from whole blood, particularly when less than 0.5 milliliters of blood are used.

BACKGROUND OF THE INVENTION

Products based on blood are of three distinct types: the cellular constituents of blood including erythrocytes, leukocytes, and platelets; the non-cellular constituents identified as either plasma or serum; and whole blood containing both the cellular and non-cellular constituents together.

Of major interest are the non-cellular constituents of blood, plasma and serum, which differ !rom one another only in the presence or absence of clotting factors. These non-cellular fluids are composed of water, dissolved salts, fats and lipids, proteins, enzymes, and a variety of subprotein groups. In particular, the chemical entities present in plasma and serum vary markedly in concentration, molecular weight, shape, size, chemical reactivity, and source of origin. In addition, the various fractions of plasma and serum have great value as therapeutic agents, as diagnostic indicators, and as a source of blood based products for in-vitro culture.

The separation of the non-cellular constituents from whole blood, particularly in volumes less than 0.5 milliliters, was previously and remains a tedious, time consuming, and complex process. The valuable components of plasma and serum, such as blood protein fractions, have a tendency to be fragile and are easily denatured; and unintended protein denaturization can result from shifts in pH, osmolality, temperature, and pressure. For these reasons, the separation of plasma and serum from whole blood is typically performed only in two ways: centrifugation and filtration.

Centrifugation (and its counterparts of sedimentation and precipitation) is primarily useful when relatively large volumes of whole blood are required to be separated. Typically, at least 10 milliliters of whole blood are required for effective centrifugation. This quantity of whole blood is required also when blood is allowed first to coagulate into a clotted mass before being able to draw off any useful quantity of serum as the separated fluid. Although a wide variety of apparatus and techniques are conventionally available, the centrifugation process of separation always relies exclusively upon the mass of the cellular constituents and the force of acceleration to achieve a separation of cellular and non-cellular constituents.

The alternative means for separating plasma or serum from whole blood is filtration. Unfortunately, the conventional materials and known mechanisms of action employed within general methods of filtration have proven not to be either useful or effective for separation of whole blood. This is best understood by a summary review of the three fundamental filtration mechanisms now generally available. These are: surface filtration (or two-dimensional sieving); depth filtration (or three-dimensional sieving); and adsorptive filtration.

Filters are typically classified according to the mechanism of filtration by which they operate, although most filters do not operate purely by a single mechanism of action; rather, the mechanism which dominates is frequently dictated by the size of the particles being filtered out. Surface filtration (or two-dimensional sieving) will invariably remove large particles (typically greater than 100 microns) at the surface. The requirement for this filter mechanism to function is simply that the pores or holes on the exterior surface or face of the filter be smaller than the particles which are to be removed. Some particles only a little smaller in size than the diameter of the pores will also be removed by surface filtration because of bridging effects. A thin perforated plate is an example of a filter which will operate only by surface filtration; however, if the perforated plate is composed of many layers of particles or fibers, then depth filtration may also occur to some degree in combination with surface filtration.

Alternatively, depth filtration (or three-dimensional sieving) is a filtration mechanism which occurs when the particles to be retained actually penetrate into the interior of the filter medium (fiber or particulate) and become entrapped in the tortuous internal passages within the thickness of the filter material itself. As the particle (or cell) travels through the many internal passages and pathways within the thickness of the filter material, the individual particle (or cell) becomes retained and removed from the carrying fluid when it tries to pass through an orifice smaller in size than itself. While surface filters require very fine fibers in order to remove medium (100—10 microns) and small (10.0—0.1 microns) particles or cells efficiently, depth filters can remove the same sized particles (or cells) using fibers rather less fine because an actual penetration of the filter material occurs. A depth filter is therefore like several inefficient surface filters in series, each layer removing only a proportion of the particles (or cells) from the liquid carrying them. Increasing the thickness of a depth filter thus generally increases its efficiency of separation.

Finally, adsorptive filtration is a mechanism which involves the removal of particles (or cells) from a liquid when the particles (or cells) come into contact with and become physically adsorbed to the internal surfaces of the filter material. This filtration mechanism does not rely upon sieving; rather, it removes particles (or cells) which are smaller in size than the pores within the filter material. There is thus no effective limit to the smallness of the particles (or cells) which can be removed; and very small particles (typically 0.1 um) are removed with high efficiency by filters employing this mechanism of action. Instead of sieving, adsorptive filtration requires an affinity by the particle (or cell) for the filter material such that adhesion of on ®to the other occurs readily. The thickness of the adsorptive filter provides multiple layers, each of which physically adsorbs a proportion of the particles (or cells) and removes them from the carrying liquid. An efficient adsorptive filter will present a large internal surface area to the particles (or cells) such that the probability of adsorptive capture becomes very high.

There are two types of forces Which operate beTween a particle (or cell) and the adsorptive filter medium which dictate whether the degree of adhesion necessary for adsorptive filtration to occur will take place: Van der Waal's forces which are relatively weak and only operative over very short distances (approximately 10 Angstroms); and electrostatic forces which are relatively strong because most solids acquire a surface electrical charge when brought into contact with polar liquids. The latter is by far the more important of the two.

Electrostatic forces and charges usually originate either by the preferential dissolution of a component ion from the solid phase, thus leaving an excess of the opposite charge on the surface of the solid; or by the preferential adsorption of a counter-ion from solution onto the surface of the solid. The overall net charge of the solid material can be either positive or negative in sign (polarity); and the magnitude of the polar charge is typically expressed as an electrical potential. The net electrical potential of a solid surface cannot be measured directly but a closely related quantity commonly known as the "zeta potential" can be determined empirically by any of four different, conventionally known, electrokinetic techniques. Regardless of how they are measured, surfaces with an electrostatic charge of the same sign (polarity) repel each other while surfaces of opposite electrical charge attract each other. The attraction of oppositely charged surfaces for each other is the constant requirement, underlying basis, and mechanism of action for adsorptive filtration. The adsorptive material comprising the filter itself always has a demonstrable surface electrical charge which is opposite in polarity to the surface electrical charge in comparison with the particle (or cell) to be separated and retained [Wnek, W., *Filtration & Separation* 11:237–242 (1974); Raistrick, J.H., *Filtration & Separation* 13:614–620 (1976); and Shackleton and Chem, *Filtration & Separation* 14:632–638 (1977)].

As regards the practice of filtering whole blood into cellular and non-cellular constituents, the presently available filters for this purpose conventionallY employ either a surface or depth filter mechanism. Filters representing the use of the surface filtration mechanism are described within U.S. Pat. Nos. 3,552,925 and 3,552,928. Filters representing the use of the depth filtration mechanism are disclosed by U.S. Pat. Nos. 4,246,107 and 3,448,041. Such filters and filtration mechanisms, however, are conventionally recognized as being ineffective for separating small volumes of whole blood. These filters clog easily and/or fail to separate cellular and non-cellular constituents effectively. The most recent advance in whole blood filtration is described by U.S. Pat. No. 4,477,575 which employs glass fibers within a prescribed diameter and density range for separating small volumes of whole blood. The filtration mechanism employed with these glass fiber filters is not described or characterized within the text of the patent. However, the capacity and utility of the glass fiber filter system appears to be limited by the requirement that the total volume of the plasma or serum to be separated from whole blood be at most 50% of the absorption volume of the glass fiber layer.

Accordingly, insofar as is presently known, there are no examples of either adsorptive filters or the adsorptive filtration mechanism being employed for separation of whole blood into constituents. Rather, it appears that the complexities and difficulties of controlling the overall net electrical surface charge for the filter material and the effects of purposefully imposing an electrical charge upon the cellular and non-cellular constituents of blood have been viewed as being too demanding, variable, and intricate for effective filtration to be achieved using an electrically charged filtration mechanism.

SUMMARY OF THE INVENTION

The present invention provides a blood filter for rapid and effective separation of cellular and non-cellular constituents from whole blood, especially for a blood sample less than 0.5 milliliters in volume, this filter comprising: a porous matrix having a plurality of external and internal surfaces and comprised of at least one composition having an overall negative surface electric charge when in contact with the whole blood sample. Preferably, the matrix composition is crystalline in structure and is substantially chemically non-reactive with the constituents of whole blood. The porous matrix is desirably present as a mass of definable configuration and dimensions and has a bulk density ranging between 1–2.0 grams per cubic centimeter.

The present invention also provides a method for rapid and effective separation of whole blood into cellular and non-cellular constituents, especially for blood samples less than 0.5 milliliters in volume, this method comprising the steps of: obtaining a porous matrix having a plurality of external and internal surfaces and comprising at least one composition having an overall negative electrical surface charge at blood pH values; introducing a blood sample to one external surface of the porous matrix; waiting a determinable period of time for the blood sample to become separated into cellular and non-cellular constituents by the porous matrix; and collecting the non-cellular constituents of the blood sample from another external surface of the porous matrix.

BRIEF DESCRIPTION OF THE FIGURES

The present invention can be more easily and completely understood in conjunction with the accompanying drawing, in which:

FIGS. 1a–1g are representations of each of the seven classes of crystal unit cell structures.

DESCRIPTION OF THE PREFERRED EMBODIMENTS

Figure 2B:
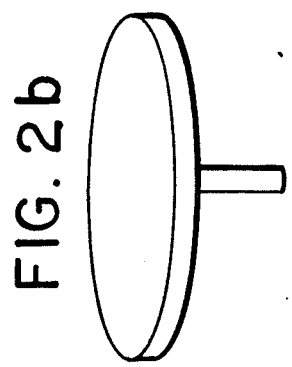
FIGS. 2a–2e are representations of different separation bed configurations for the blood filter of the present invention.

In its most basic form, the present invention is a unique filter material and medium for the rapid and effective separation of cellular and non-cellular constituents from a sample of whole blood which is typically less than 0.5 milliliters (hereinafter "ml") in volume, and preferrably less than about 50microliters (hereinafter "uL") in volume. This filter material can be positioned in a supporting container as a filtering apparatus and is most desirably employed in a method for filtering whole blood vol m in the r from 10–50 uL.

This blood filter material, apparatus, and methodology provides a number of major benefits and advantages to the user not previously available or forseeable in the relevant art. These include:

(1) The ability to efficiently separate whole blood, especially volumes in the range from 0.5 mL –5.0 uL;

(2) The ability to efficiently remove the cellular constituents (erythrocytes, leukocytes, and platelets) without causing cell injury or rupture;

(3) Efficient separation of whole blood volumes rapidly, typically within 30 seconds duration from beginning to end;

(4) Highly efficient recovery of individual fractions ranging between 85-95% from plasma and/or serum filtrates. For example, theophylline can be recovered at greater than 95% efficiency compared to a centrifuge separated sample;

(5) There is no change of plasma or serum concentration as a result of using the present invention to separate whole blood; there is thus no water absorption or concentration loss due to evaporation as a result of passing through the filter medium; and (6) There is no requirement for dilution of the whole blood sample in order to avoid coagulation or clogging of the filter.

The blood filter of the present invention is a porous matrix having a plurality of exterior and interior surfaces and comprised of at least one composition having an overall negative surface electrical charge at blood pH values. It is preferred that the matrix material be crystalline in structure; have a bulk density ranging between 0.1-2.0 grams per cubic centimeter; and be physically present as a three-dimensional porous mass of definable configuration and dimensions. There are, therefore, a variety of different parameters and characteristics desirably presented by the filter material for optimum separation of whole blood. In order to more easily and completely understand the requirements and advantages of the present blood filter material, apparatus, and methodology, each of these characteristics and parameters will be described individually in detail.

The Physical State And Structural Limitations Of The Blood Filter Matrix Material The physical state and structure of the porous matrix material serving as the blood filter can take several different forms: as a crystalline solid without any silicates; as a crystalline solid containing some silicates; and as an amorphous solid without silicates.

A crystalline solid is a solid mass in which the composite atoms or molecules are arranged in a regular manner or arrangement repeated in identical fashion. When formed, a crystalline mass is bounded by plane surfaces or faces intersecting at set angles along three axes to form what is typically termed a "lattice structure." This regular geometric arrangement or lattice structure is always a polygon and conforms to a crystal unit cell structure and stoichiometry of which there are seven recognized classes or systems. A crystalline composition or substance need not necessarily appear in the form of crystals; however, it always presents a regular, repetitious structural format and arrangement which conforms to one of the basic seven crystal unit cell structures.

The basic seven crystal classes are identified by Table 1 and FIGS. 1a–1g respectively.

A crystalline composition or matrix material is different and distinguishable from a glass — which is, by definition, not in a crystalline state. A glass is a hard, amorphous and brittle substance made by fusing together one or more of the oxides of silicon, boron, or phosphorous with certain basic oxides (e.g., sodium, magnesium, calcium, or potassium); and cooling the resulting product rapidly to prevent crystallization or devitrification. A glass, therefore, is always in the vitreous state and never in a crystalline physical state. Moreover, although glass is typically composed of a mixture of silicates and often is made by melting silica ($SiO_4$) with various oxides and/or carbonates, pure silica itself is not a glass. To the contrary, silica exists in not less than three crystalline forms: quartz, tridymite, and crystobalite — each of which has an individual and different crystal unit cell structure from the others. In crystobalite, the $SiO_4$ is tetrahedral arranged in a diamond-like lattice structure. In the quartz and tridymite forms, the arrangement of the tetrahedral structure has a screw like pattern; there can be "right-handed" and "left-handed" forms, each of which is a mirror image of the other rotating a plane of polarized light in an opposite direction. However, if pure crystalline silica is melted (1,710 C.), then a highly viscous liquid is obtained which when if supercooled will form "quartz glass" — an amorphous, vitreous solid.

A very few silicates structurally are neither a glass nor a crystalline solid. For example, the composition commonly called "water glass" ($Na_2SiO_3$) is a jelly-like compound whose generic chemical name is sodium metasilicate. Pure Water glass is colorless and readily dissolves in water. Accordingly, the mere presence of silica in detectable quantities within a material or formulation, does not in and of itself dictate or influence the physical state and structure of the composition itself. Silica containing compositions may exist in a crystalline state; as an amorphous (vitreous), glass; or in a physical state which is neither crystalline nor a glass.

For purposes of the present invention, it is most preferred that the substances employed as filtering materials, regardless of chemical composition, exist and be present in a crystalline state. Crystalline silicates comprised of silicon, oxygen, and metallic and non-metallic elements such as naturally occurring rocks, including talc, zircon, asbestos, mica, beryl, carnelian, etc. (as described in *Inorganic Chemistry: Principles Of Structure And Reactivity*, J.E. Huhee, 1983) are deemed to be within the scope of this invention by reason of the crystalline structure of the solid. Naturally occurring rocks such as osidian, hematite, and quartz glasses are deemed to be outside the scope of this invention. Similarly, any silica-containing substance which exists in a solid state as either an amorphous glass or any other non-crystalline structural mass is also outside the scope of the present invention.

TABLE 1

| CRYSTAL CLASS | DIMENSIONS | ANGLES | EXAMPLES |
|---|---|---|---|
| cubic | $a = b = c$ | $\alpha = \beta = \gamma = 90°$ | Ag, NaCl |
| tetragonal | $a = b \neq c$ | $\alpha = \beta = \gamma = 90°$ | Sn (white), $MgF_2$ |
| orthorhombic | $a \neq b \neq c$ | $\alpha = \beta = \gamma = 90°$ | $S_8$, $HgCl_2$ |
| rhombohedral | $a = b = c$ | $\alpha = \beta = \gamma \neq 90°$ | $Al_2O_3$ |
| hexagonal | $a = b \neq c$ | $\alpha = \beta = 90°, \gamma = 120°$ | Mg, CuS |
| monoclinic | $a \neq b \neq c$ | $\alpha = \gamma = 90°, \beta \neq 90°$ | $KClO_3$ |
| triclinic | $a \neq b \neq c$ | $\alpha \neq \beta \neq \gamma \neq 90°$ | $CuSO_4 \cdot 5H_2O$ |

A Filter Matrix Material Having An Overall Negative Surface Electrical Charge As concerns the present invention, the ability to separate and effectivelY retain red blood cells, white blood cells, and platelets while allowing the proteinaceous plasma or serum fluid to pass through correspond directly with an electrical charge surface phenomenon known as "zeta potential." [Kryut, H.R., "Colloid Science", Volume 1, Elsevier Publishing Company, Amsterdam, 1952.]The overall net electrical charge of any composition or substance is caused by the chemical constituents present at the surface and their interactions with $H^+$ and $OH^-$ ions in the aqueous phase which cause an overall electrical charge of either negative or positive value. This principle has been established for techniques of filtering beverages and other aqueous liquids using refractory fibers bearing a positive electrical charge in order to adsorb negatively charged particles which come into contact with and adhere to the positive charge surface of the filter material. Traditionally, the positively electrically charged fibers such as asbestos and alumina attract the negatively charged entities and hold them on the surface of the fiber by electrostatic forces while allowing the carrying fluid to pass. The use of a positive zeta potential via positively charged refractory fibers able to adsorb negatively charged particles in a fluid is the conventional basis and mechanism of action for adsorptive filtration as previously described herein.

Contrary to the conventional principles of adsorptive filtration, the present invention demands and requires that the material comprising the porous filter matrix present and maintain a net negative electrical surface charge over the range of pH values (typically pH 4.0–8.0) provided by whole blood. It will be clearly and explicitly understood that the composition or formulation of the filter material can provide the requisite overall negative electrical surface charge inherently; or be modified via the inclusion and use of pH additives to create and maintain an overall negative surface electrical charge for the filter composition.

The requirement for an overall negative surface electrical charge on the compositions serving as the blood filter matrix material is contrary to accepted practice and mechanism of action for adsorptive filtration; and stands contrary to traditional requirements in the art regarding an effective capability to separate cellular constituents from whole blood. Adsorptive filtration relies and depends upon the attraction of oppositely char9ed molecules for filtration to occur. In each instance, the adsorptive filter material is positively charged; and the greater the positive electrical charge value on the surface of the filtering material, the more effective the separation and filtration of the adsorptive filter system [Wnek, W., *Filtration & Separation* 11:237–242 (1974) and the references cited therein]. Similarly, investigations have revealed that red blood cells, white blood cells, and platelets each demonstrate a negative net electrical surface charge at pH values as low as 3.25 [*Electrical Phenomena At Interfaces* (Kitahara and Watanab, editors), Marcel Dekker, Inc., New York, 1984, pages 398–412]. Clearly, therefore, all the cellular constituents of whole blood will demonstrate an overall negative electrical charge on their surfaces under in-vivo or ex-vivo conditions. Accordingly, because the material of the blood filter matrix comprising the present invention is required to present a negative net surface electrical charge over all whole blood pH values; and because the cellular constituents of whole blood in-vivo and ex-vivo will always provide a net negative surface electrical charge, it is clear that the filtration mechanism of action between the negatively charged blood filter material and the negatively charged cellular constituents is one of electrical charge repulsion rather than of attraction. The creation and use of similarly charged electrostatic forces for repulsion and regress of cells rather than the use of oppositely charged forces for attraction and absorption of surface charged entities is singular and unique in a filter material and methodology for the separation of whole blood.

Chemical Compositions Presenting A Negative Electrical Surface Charge

The preferred embodiments of compositions and substances able to demonstrate an overall negative surface electrical charge at normal and abnormal whole blood pH values are the crystalline metallic oxide compositions conventionally known and commercially available as refractory fibers. The desirable fiber compositions include: fibers constituted primarily of either alumina or zirconia marketed under the trademark "Saffil" (Imperial Chemical Industries Ltd.); chrysotile asbestos fibers (washed and unwashed); rutile titania and a variety of mixed oxide compositions including $Y_2O_3$, $Ta_2O_5$, $HfO_2$, $TiO_2$, $Al_2O_3$, $CeO_2$, and rare earth oxides marketed generally under the trademark "Zircar" (Zircar Products, Inc.). In addition, other crystalline metallic oxides and a variety of different mineral salts, sulfide compositions, and elements, as well as mixtures of all these prepared in porous matrix form are able also to provide the requisite overall negative electrical surface charge at all useful pH values for separation of whole blood constituents. This is illustrated by the data of Table 2 below.

It is expected also that a variety of synthetic compositions in monomeric and polymeric form which have the requisite overall negative surface charge can also be prepared and used to advantage. Accordingly, all compositions, regardless of chemical formulation and individual form, which demonstrate the negative surface charge characteristics are deemed to be within the scope of the present invention.

TABLE 2

| | NEGATIVE NET ELECTRICAL CHARGE AT PH VALUES |
|---|---|
| METALLIC OXIDES | |
| $Al_2O_3$ | greater than 9.0 |
| $TiO_2$ | greater than 6.7 |
| $ZrO_2$ | greater than 4.8 |
| $Fe_2O_3$ | greater than 5.0 |
| $SnO_2$ | greater than 4.5 |
| MgO | greater than 12.0 |
| MINERAL SALTS | |
| $SrSO_4$ | greater than 2.3 |
| $BaSO_4$ | greater than 3.4 |
| $AlPO_4$ | greater than 4.0 |
| $MgCO_3$ | greater than 4.0 |
| $CaCO_3$ | greater than 8.0 |
| SULFIDES | |
| ZnS | greater than 8.0 |
| $MoS_2$ | greater than 3.0 |
| ELEMENTS | |
| S | greater than 3.0 |

The preferred metallic oxide compositions are commonly available in a variety of different formats Most preferred are fibers having diameters of between 0.5–6 microns. Alumina, zirconia, and titanium dioxide are preferably employed as a mass of fibers whose diameter size are within the 0.5–6 micron range. Alternatively, fibers with diameters outside this preferred range are deemed useful in varying degrees. It will be recognized and appreciated also that metallic oxide compositions such as magnesium, silicate (talc), and magnesium carbonate can be employed in other physical formats including granular particles and woven textile fabrics. When employed in particulate powder form, the particles are preferrably in the range from 0.1–5.0 microns in size. Moreover, when the particulate powder form is employed for making the blood filter, it is expected to improve the mechanical strength of the filter matrix. In addition, known binding agents can be used with fibers alone or in combination with particulate powders to form a porous mass of definable configuration and dimensions. Such binding agents aid in seating and positioning the blood filter matrix material in a container to form a filter apparatus. The desirable binding agents are typically solutions or water-based emulsions which can be admixed with the fibers or particulate powder to form a porous mass, followed by complete drying. Some preferred binding agents are waterglass, polyvinyl acetate, polyvinyl propionate, and polyacrylic acid esters whose use is conventionally known in this art.

It is also recognized that the preferred crystalline metallic oxide compositions can be obtained as woven textile fibers which typically take form as non-woven felts, mats, or papers; and as woven cloths and weaves. The woven textile formats are deemed to be less desirable for use as blood filter material in view of their limited bulk densities. The preferred range of bulk density lies between 0.1–2.0 grams per cubic centimeter. This bulk density range is deemed optional but desirable in order to provide a porous mass with a sufficiency of depth, pores, and internal surface area such that the repulsion phenomenon between the overall negative electrical surface charge of the filter material is able to cause a physical repulsion, regress, and consequential retention of the negatively charged cellular constituents of whole blood within the filter mass. Alternatively, it is recognized that many of these woven textile formats can be prepared in a thickness and bulk density sufficient to provide an effective blood filter medium. Under these circumstances, the woven fabric nature of the metallic oxide composition forming the blood filter material is expected to function more effectively to separate the cellular and non-cellular constituents of whole blood.

It is also recognized that not all metallic oxides, mineral salts, and sulfides, alone or in combination, will be able to demonstrate the requisite negative surface electrical charge at whole blood pH values of about 4.0–8.0. To aid in presenting and maintaining not only an overall net negative electrical surface charge at the lower and middle pH ranges, but also in those instances where it is desirable to induce an enhanced negative surface electrostatic force, the use of pH additives is highly recommended and desirable. Such pH additives are to be admixed with the metallic oxide, mineral salts, or sulfide compositions to increase and enhance the negative zeta potential of the filter matrix material. A wide range of inorganic and organic materials may be employed as pH additives for enhancement of negative surface charge. Preferred are three alkaline materials: sodium metasilicate in concentrations ranging from 0.1–3.0%; sodium bicarbonate in concentrations ranging from 0.01–0.1%; and sodium phosphate buffers commonly used in blood analyses.

Desirable Bulk Density For The Porous Filter Matrix

The bulk or bed density is a meaningful parameter of the filter material formed as a porous mass. In combination with the diameter of the fiber or the size of the particulate in the powder, the bulk density serves as one means of defining the effective pore sizes; of controlling the diameter and length of the internal passages and flow pathways within the thickness of the filter material; and maintaining the effectiveness of the negatively charged repulsion forces on the internal surfaces. It is recognized that negative surface electrical charge forces operate and are effective over relatively short distances. Such electronegative surface charges, therefore, cannot be expected to effectively repel the negatively charged cellular constituents of blood and to prevent them from passing through the filter matrix material when the pores, internal passages, and internal surfaces are widely spaced or dimensioned. A sufficient bulk density, therefore, not only meaningfully influences the effective depth and thickness of the porous mass comprising the filter material; but also dominates and controls the surface repulsion filtering mechanism by which effective separation of whole blood is made.

Empirical investigations have also demonstrated an inverse correlation and trade-off between bulk density and the speed of whole blood separation. Very high bulk densities for the porous mass tend to substantially reduce the speed of separation. Very high bulk densities also change the mode and mechanism of separation from one of electrical charge repulsion between the surface of the filter matrix material and the blood cells (whereby the pores and passageways in the filter are held open for the flow of fluid by repelling the negatively charged cellular constituents) into one of conventional mechanical filtration or sieving in which the blood cells block access to most of the pores and internal passageways within the filter mass and prevent the flow of fluid through the thickness of the matrix material. Alternatively, a very low bulk density fails to provide sufficient internal passages, flow paths, and overall negative surface electrical charge to cause a useful separation. For these reasons, recognizing that speed is a most desirable feature when separating whole blood; and to avoid destroying the repulsion phenomenon provided by negative surface charge forces—it is preferred that the bulk density of the porous mass, regardless of configuration or specific dimensions, be within the range of 0.1–2.0 grams per cubic centimeter and most desirably be in the range from 0.4–1.0 grams per cubic centimeter. It will be appreciated that the most preferred embodiments will employ the middle values of this specified range.

Figure 2E:
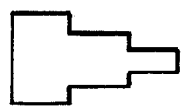
Figure 2A:
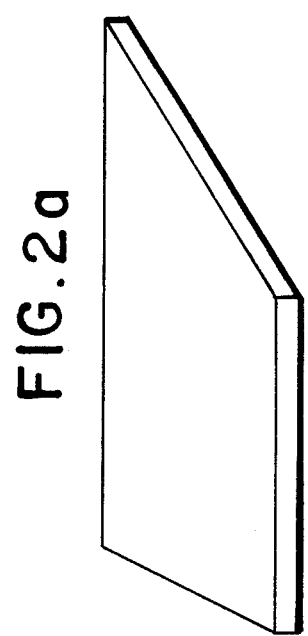
Figure 2D:
Figure 2C:
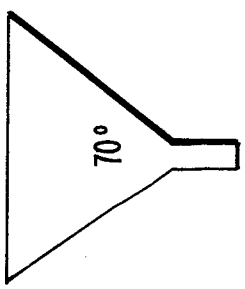

The physical or mechanical configuration of filter material (conforming to the bulk density requirement of from 0.1–2.0 grams per cubic centimeter) has also been demonstrated to influence the speed of whole blood separation. The blood filter materials, apparatus, and methodology of the present invention provide a blood filter which functions in many respects as a wick. For this reason, a variety of different wicks and wicking bed configurations have been developed as illustrated by FIGS. 2a–2e. Each configured porous mass was inserted into a support such as a container whose internal configuration and dimensions conformed at least in part to the shape of the wicking bed. Each supporting container comprised at least one solid wall to form an article with an internal lumen; a first open end for introduction of a Whole blood sample into the internal lumen of the article; and a second open end for the collection of non-cellular fluid from the internal lumen of the article. Each porous mass comprising the blood filter wick material in a specific bed configuration was then inserted into and positioned within the spacial volume provided by the internal lumen of the individual supporting container. Each article thus functioned as a molded filter holder apparatus for evaluating the different wicking bed configurations of FIG. 2 using identical materials as the filter matrix. FIG. 2a illustrates a rhomboid-shaped wick configuration; FIG. 2b represents a mushroom-shaped wicking configuration; FIG. 2c represents a wide-shaped cone wick configuration having an internal angle between 55–70 degrees; FIG. 2d represents a narrow-shaped wicking cone having an internal angle of approximately 11 degrees; and FIG. 2e represents stepped cylinder wicking configurations generally regardless of actual dimensions.

In all instances, the mechanical strength and integrity of the configured filter material was improved by the use of binding agents (such as polyvinyl acetate) which increased the speed of blood separation and diminished the bypassing of whole blood betWeen the edge of the porous mass and the molded container Wall which held and positioned it. Based on experimental evaluations, the optimum separating bed configuration for the porous mass is a cone of approximately 35 degrees of internal angle which provides for extremely rapid separation of cellular and non-cellular constituents without detachment of the filter matrix from the wall of the holding container. Wider cone configurations of 55 degrees and greater provided a faster rate of separation but were found to cause bypasses of whole blood more frequently; in comparison, narrower cone configurations of 15 degrees and less were found to be slower in separating whole blood and demanded more careful attention during use. These experiments therefore unequivocally demonstrate that the mechanical strength or physical configuration of the porous mass serving as the blood filter material is not a dominant or decisive factor for the present invention. To the contrary, the shape or dimensions of the porous mass comprising the filter material is at best a secondary consideration for optimizing the speed of separation; and is not a parameter of importance to the phenomenon of separation via the repelling negative electrical surface charge mechanism of action by Which the present invention functions. Accordingly, any configuration and dimensions for the filter matrix material are deemed to be within the scope of the present invention.

Filter Matrix Material Which Is Non-Reactive With Blood Constituents

In view of the invention's intended use as a blood filter material to yield serum or plasma for clinical or diagnostic assays, it is most desirable that the substance(s) employed as the filter matrix material be substantially non-reactive, chemically and immunologically, with the cellular and non-cellular constituents of whole blood. For example, it is now a common diagnostic procedure to test for the concentration of theophylline in an individual's blood as a part of his therapeutic regimen. It is recognized, therefore, that there should be as little interaction as possible between the theophylline fraction in the blood sample and the composition comprising the porous filter matrix. Moreover, it is highly desirable that the filter not bind With or retain any theophylline such that the quantitative amount subsequently determined to be present in the separated plasma or serum is in fact a true and accurate measure of the theophylline present in-vivo. For this reason, the crystalline metallic oxides are most preferred as the blood filter matrix material in view of their excellent capability to withstand and avoid non-specific binding with theophylline as well as with other non-cellular fractions of blood. This is demonstrated by the following experiment.

Example 1

8.0 mg of alumina fibers, 2–4 microns in diameter, were saturated with 16 uL of 0.1% aqueous sodium silicate to improve the physical strength of the resulting porous wick and to increase the pH of the filter matrix. The mixture of fibers and binder was partially dried; compacted to a density of 0.4–0.5 g/cc in a 55 cone-shaped configuration; and then fully dried over a 16 hour time period. This served as the filter matrix material for the experiment.

To demonstrate the attributes of this prepared filter matrix material, the following reagents and materials were used:

(1) Radiotagged theophylline: (Commercially available as a custom order from Amersham Corporation, 2636 South Clearbrook Drive, Arlington Heights, IL 60005.) Specifically used was Theophylline [14C], CFA.547 batch 15 having a specific activity of 51 mCi/mmol (1.89 GBq/mmol). The theophylline was received as a dry powder.

(2) ELISA buffer consisting of deionized water with:
   10 mM sodium phosphate
   150 mM sodium chloride
   0.1% sodium axide
   0.1% Tween 20 (3M)
   5 mg/ml bovine serum albumin
   pH adjusted to 7.2 and filtered to 0.2 um.

The dry theophylline powder was first added to 20 uL of ELISA buffer. This solution was then added to 1.5 ml of freshly collected sample of whole, heparinized blood. Non-radioactive theophylline was then added to the blood mixture bringing the total theophylline concentration to 15 ug/ml.

The radiotagged blood sample was then split into two parts: Part A to be used, as is, and passed through the blood filter; and the other Part B to be centrifuged conventionally and the plasma isolated from the blood cells, for use as a control (hereinafter "spun plasma").

All beta particle disintegration measurements of Parts A and B were made on the Tracor Analytic Mark III No. 6881 liquid scintillation counter using the BIO-FLUOR scintillation cocktail Research Products, 549 Albany Street, Boston, MA 02118.

Each Part A blood sample was applied to the upper external surface of the filter and allowed to pass through the thickness of the porous filter matrix. The filtrate was collected from the lower exterior surface of the filter with a microcapillary pipet. Proper assembly of the filter is critical to prevent bypassing by the blood sample, as trace amounts of red cells appear to artificially depress the count rate.

A measurement of both spun plasma (Part B) and filtrate (Part A) was made with the above equipment and procedures, to compare the empirical determinations of theophylline recovery from each blood sample. The data presented in Table 3 is representative of the results obtained using the alumina filter matrix material and a sample volume of 1.0 uL as the test aliquot.

TABLE 3

| TRIAL | PART B | PART A |
|---|---|---|
|  | (counts per minute) | |
| 1 | 6,375.8 | 6,068.0 |
| 2 | 6,366.4 | 5,813.0 |
| 3 | 6,240.0 | 6,660.8 |
| 4 | 6,588.8 | 6,127.1 |
| 5 | 6,238.9 | 5,795.4 |
| 6 | 6,419.5 | 5,800.0 |
| 7 | n.d. | 6,282.6 |
| Average | 6,386.6 | 6,078.1 |
| Std. Dev. | 105.9 | 295.5 |
| C.V. (%) | 1.7 | 4.9 |
| Recovery | — | 95.2% | n.d. = not determined
Std. Dev. = standard deviation
C.V. = coefficient of variation Example 2

The following two reagent enzyme assay system was used: (Available from Syva Company, palo Alto, CA 94304, tradename is tthe EMIT theophylline assay.)

(1) Reagent A (6.0 ml) sheep antibodies to theophylline, glucose-6-phosphate (G-6-P), nicotinamide adenine dinucleotide (AND), 1-methylxanthine, 0.055 mol/L Tris-HCl, pH 5.2.

(2) Reagent B (6.0 ml theophylline labelled with glucose-6-phosphate, dehydrogenase (G6P-DH), 0.055 mol/L Tri buffer, pH 8.0.

(3) Buffer concentrate (13.3 ml) 0.825 mol/L Tris buffer, pH 8.0.

(4) Calibrators (six 1.0ml vials) 0, 2.5, 5.0, 10, 20, 40 ug/ml theophylline in human serum.

The serum determination was carried out using a commercially available automatic clinical chemistry analyzer (hereinafter "Roche COBAS FARA") with the following adjustments: temperature, 37° C.; filter, 340 nm; t -time delay, 30 seconds; interval, 10 seconds; test code, THEO; Reagent A volume, 300 uL; equipment sample volume, 3 uL; diluent A volume, 35 uL; Reagent B volume, 40uL; diluent B volume, 5 uL.

The fluid to be passed through the filter matrix of Example 1 and subsequently collected and measured was a serum based control (available from Fisher Scientific, Orangeburg, NY 10962, No. 2847-31 Therma-Chem-Plus). A mid-range Level 2 control of known concentration.

The test procedure is similar to that described in Example 1; however, in this instance, the original 3.0 uL filtrate volume provided three 1.0 uL test aliquots for evaluation in each trial. The removal of individual 1 uL volumes was made three times consecutively to evaluate the effect of filtrate volume on theophylline recovery. Each 1.0 uL aliquot was evaluated in the COBAS FARA program.

The results were compared from both the applied serum and collected serum, for determination of theophylline recovery from the separator. The data presented in Table 4 is representative of the results obtained.

TABLE 4

| TRIAL | CONTROL | 1ST uL VOLUME | 2ND uL VOLUME | 3RD uL VOLUME |
|---|---|---|---|---|
| A | 13.43 | n.d. | 12.59 | 13.52 |
| B | 12.69 | 11.63 | 12.22 | 12.94 |
| C | 12.23 | 13.33 | 12.58 | 12.98 |
| Average | 12.78 | 12.48 | 12.46 | 13.15 |
| Std. Dev. | 0.61 | 0.85 | 0.17 | 0.26 |
| C.V. (%) | 3.9 | 6.8 | 1.4 | 2.0 |
| Recovery | — | 97.6% | 97.5% | 102.8% |

Std. Dev. = standard deviation
C.V. = coefficient of variation
n.d. = not determined As the empirical data reveals, 100% of the total theophylline was present in the filtrate.

In order to more generally avoid non-specific binding to the filter material by the non-cellular constituents in plasma and/or serum, it is highly desirable that one or more blocking agents be added to the filter matrix material. Such agents include: cholic acid; deoxycholic acid; and heparin. The concentration of blocking agent to be added to the filter material is preferably in the range from 0.001–0.1% by weight. The use of such blocking agents in general are expected to aid in avoiding non-specific binding of the desired non-cellular blood fractions and allow them to pass through the filter material without being retained.

The present invention is not to be restricted in form nor limited in scope except by the claims appended hereto.

What we claim is:

1. A method for rapid and effective separation of cellular and non-cellular constituents in a blood sample, said method comprising the steps of:
   obtaining a porous matrix expressing a negative electrical surface charge, said porous matrix having a plurality of internal and external surfaces comprised of at least one crystalline composition having an overall negative electrical surface charge;
   introducing a blood sample to an external surface of said negatively charged porous matrix;
   waiting a determinable period of time for said introduced blood sample to become separated into cellular and non-cellular fractions by interaction with at least the negative electrical surface charge of said porous matrix; and
   collecting at least one of said separated fractions.

2. A method for rapid and effective separation of cellular and non-cellular constituents in a blood sample, said method comprising the steps of:
   obtaining a porous matrix expressing a negative electrical surface charge, said porous matrix having a plurality of internal and external surfaces comprised of a composition formulated without silicates and having an overall negative electrical surface charge;
   introducing a blood sample to an external surface of said negatively charged porous matrix;
   waiting a determinable period of time for said introduced blood sample to become separated into cellular and non-cellular fractions by interaction with at least the negative electrical surface charge said porous matrix; and
   collecting at least one of said separated fractions.

3. The method as recited in claim 1 or 2 wherein said porous matrix comprises at least one metallic oxide.

4. The method as recited in claim 1 or 2 wherein said porous matrix comprises at least one composition selected from the group consisting of mineral salts and sulfides.

5. The method as recited in claim 1 or 2 wherein said porous matrix has a bulk density ranging from 0.1-2.0 grams per cubic centimeter.

6. The method as recited in claim 1 or 2 wherein said porous matrix has a bulk density ranging from 0.4-1.0 grams per cubic centimeter.

7. The method as recited in claim 1 or 2 wherein said porous matirx is substantially chemically non-reactive with constituents of the blood sample.

8. The method as recited in claim 1 or 2 wherein said porous matrix further comprises a binding agent.

9. The method as recited in claim 8 wherein said binding agent is selected from the group consisting of polyvinyl acetate, polyvinyl propionate, and polyacrylic acid esters.

10. The method as recited in claim 1 or 2 wherein said porous matrix further comprises a pH additive.

11. The method as recited in claim 10 wherein said pH additive is selected from the group consisting of sodium metasilicate and sodium carbonate.

12. The method as recited in claim 1 or 2 wherein said porous matrix further comprises a blocking agent for reduction of non-specific binding.

13. The method as recited in claim 12 wherein said blocking agent is selected from the group consisting of cholic acid, deoxycholic acid, and heparin.

14. The method as recited in claim 1 or 2 wherein said porous matrix is comprised of fibers.

15. The method as recited in claim 14 wherein said fibers have an average diameter ranging from 0.5-6.0 microns.

16. The method as recited in claim 1 or 2 wherein said porous matrix is comprised of a particulate powder.

17. The method as recited in claim 16 wherein said particulate of said powder has an average size ranging from 0.1-5.0 microns.

18. The method as recited in claim 1 or 2 wherein said porous matrix includes at least one composition selected from the group consisting of aluminum oxide, zirconium oxide, titanium oxide, magnesium carbonate, yttrium oxide, hafnium oxide, cesium oxide, tantalum oxide, and rare earth oxides.

19. The method as recited in claim 1 or 2 wherein saaid porous matrix is prepared as a material selected from the group consisting of woven cloths, non-woven felts, papers, and mats.

20. The method as recited in claim 1 or 2 wherein said composition takes structural shape as at least one crystal unit cell selected from the class consisting of cubic, tetragonal, orthorhombic, rhombohedral, hexagonal, monoclinic, and triclinic crystal systems.

* * * * *